US00PP19007P3

(12) United States Plant Patent
McLaughlin

(10) Patent No.: US PP19,007 P3
(45) Date of Patent: Jul. 8, 2008

(54) APPLE TREE NAMED 'MCLAUGHLIN GALA'

(50) Latin Name: *Malus domestica*
Varietal Denomination: McLaughlin Gala

(76) Inventor: Robert Thomas McLaughlin, 2943 Bonser Run Rd., Portsmouth, OH (US) 45662

( * ) Notice: Subject to any disclaimer, the term of this patent is extended or adjusted under 35 U.S.C. 154(b) by 0 days.

(21) Appl. No.: 11/585,298

(22) Filed: Oct. 23, 2006

(51) Int. Cl.
*A01H 5/00* (2006.01)

(52) U.S. Cl. ..... Plt./162

(58) Field of Classification Search ..... Plt./162
See application file for complete search history.

*Primary Examiner*—Kent L. Bell
*Assistant Examiner*—S. B. McCormick-Ewoldt

(57) ABSTRACT

A new and distinct variety of apple tree, 'McLaughlin Gala,' originating as a limb mutation of the *Malus domestica* variety of 'Kidds D-8' (U.S. Plant Pat. No. 3,637). This new variety is unique from its parent because it develops and finishes fruit color to a 100% clear yellow with no red striping or blush. The new variety matures 4 to 6 days before its parent.

3 Drawing Sheets

DESCRIPTION OF RELATED APPLICATIONS

The new variety, 'McLaughlin Gala' differs from the parent and other Gala varieties in the following characteristics:

A. The fruit of the new variety is a bright, clear yellow color which differs from the parent, 'Kidds D-8' (U.S. Plant Pat. No. 3,637), and all other Gala selections.

Latin name of the genus and species of the plant claimed: *Malus domestica.*

BACKGROUND OF THE INVENTION

A new and distinct variety of Gala apple tree originating as a limb mutation of 'Kidds D-8' (U.S. Plant Pat. No. 3,637) hereinafter referred to as the 'McLaughlin Gala'. This new sport is unique from the parent because the skin of the fruit is a clear yellow color, with no red coloration. The new variety ripens 4 to 6 days ahead of the parent.

SUMMARY OF THE INVENTION

This new and distinct variety of apple was discovered in 1998 by Robert Thomas McLaughlin in Portsmouth, Scioto County, Ohio, USA. It was discovered in a producing block of 'Kidds D-8' (U.S. Plant Pat. No. 3,637) and was distinct and unique because of its clear yellow color and the fact that it ripened 4 to 6 days ahead of the parent. In August of 2001, buds were taken from the original limb and reproduced by chip budding in Brentwood, Calif., on M9 337 rootstock. (an unpatented selection) The new variety remains true to the description herein contained. The new variety has not been reproduced on its own root.

BRIEF DESCRIPTION OF THE DRAWINGS

The accompanying photographs show typical specimens of the new variety as depicted in color as nearly true as is reasonably possible in color illustrations of this character. These specimens were obtained at Portsmouth, Scioto County, Ohio, USA.

FIG. 1/3 illustrates the fruit and foliage of the new variety at maturity.

FIG. 2/3 illustrates the new variety and the parent, 'Kidds D-8' (U.S. Plant Pat. No. 3,637), both grown on the original tree.

FIG. 3/3 illustrates the blossom of the new variety.

BOTANICAL DESCRIPTION OF THE PLANT

A detailed description of the new variety follows using The Royal Society of London Colour Chart, 1986 edition.

Parentage: A limb mutation of 'Kidds D-8', (U.S. Plant Pat. No. 3,637). Locality of the original discovery and observations is Portsmouth, Scioto County, Ohio, USA.

Tree:
- *Age.*—7 years.
- *Size.*—Large, height 4 m, width, 4 m.
- *Vigor.*—Vigorous, yearly growth averages 1 m.
- *Density.*—Medium.
- *Form.*—Upright, spreading.
- *Production.*—Very productive, averaging 800 bushels per acre.
- *Growth type.*—Non-spur.
- *Bearing.*—Annual.

Trunk:
- *Size.*—17 cm in diameter at 100 cm above ground level.
- *Surface.*—Smooth.
- *Bark color.*—Gray Green 197 A.
- *Lenticels.*—Length 2 cm, width 1 cm.
- *Lenticel color.*—Grey Green 197 B.
- *Lenticel density.*—3 per $cm^2$.

Branches:
- *3 year branch.*—23 mm in diameter, color Grayed Orange 173 A.
- *2 year branch.*—8 to 10 mm in diameter, length 25 to 30 cm, colored Grayed Orange 175 A.
- *1 year branch.*—7 to 9 mm in diameter, length 30 to 45 cm, color Greyed Orange 177 A.
- *Surface.*Smooth.
- *Form.*—Profuse branching.
- *Average angle.*—50°.
- *Buds.*—Alternate, applied, length 8 mm, width 4 mm, color 185 A.

Leaves:
*Size.*—Length 38 mm, width 22 mm.
*Form.*—Ovate.
*Texture.*—Leathery, thick.
*Leaf thickness.*—3 mm.
*Base.*—Broadly cuneate.
*Apex.*—Broadly acute.
*Margin.*—Serrate.
*Pubescence.*—None on adaxial surface, fine pubescence on abaxial surface.
*Leaf color.*—Adaxial: Yellow Green 146 A. Abaxial: Yellow Green 146 B.
*Venation.*—Pinnate, 9 to 14 veins mainly alternate.
*Vein color.*—Adaxial: Yellow Green 146 A. Abaxial: Yellow Green 144 C.
*Stipules.*—2, at base of petiole on most older leaves; length: 16 mm, width 2 mm at widest point, color Yellow Green 146 A.

Petiole:
*Size.*—Length 35 to 40 mm, diameter 2 mm at junction with leaf, 5 mm at junction with branch.
*Color.*—Grayed Green 191 A to Grayed Purple 183 C at junction with branch.

Flower buds at popcorn stage:
*Pedicel.*—Length: 15 to 20 mm, diameter 2 mm.
*Pedicel color.*—Green 146 D.
*Bud.*—Length 9 mm, width 7 mm.
*Bud color.*—Slight blush of Red 56 C with background of White 155 D.

Flowers:
*Bloom timing.*—Early season.
*Bloom period.*—April 1 to 8 in Portsmouth, Ohio.
*Pollination requirements.*—Viable pollen from another fertile variety blooming in the same period such as Granny Smith (an unpatented selection), Golden Delicious (an unpatented selection), or Indian Summer crabapple (an unpatented selection).
*Number of flowers per cluster.*—3 to 5.
*Fragrance.*—Very fragrant.
*Corolla diameter.*—25 mm to 34 mm.
*Stamens.*—20 to 25 in number, color White 155 D.
*Anther color.*—Yellow 14 B.
*Pollen.*—Profuse.
*Ovary.*—Pubescent, color Grayed Green 193 A.
*Pistil.*—Slightly lower than anthers in a majority of blossoms.
*Sepals.*—5 in number, length 4 mm, width 2 mm, pubescent, color Grayed Green 193 A.
*Petals.*—5 in number, length 11 mm, width 6 mm, slightly overlapping.
*Petal shape.*—Ovate, base rounded to cuneate at junction with receptacle, apex rounded, margin very slightly ruffled.
*Petal color.*—Adaxile: White 155 D. Abaxile: White 155 D.
*Petal texture.*—Soft.

Fruit:
*Maturity when described.*—Firm ripe.
*Date of picking.*—August 5, in Scioto County, Ohio, generally harvested in one picking.
*Size.*—Axial diameter 80 mm, transverse diameter 95 mm.
*Form.*—Uniform, symmetrical, regular, reniform to chordate.
*Cavity.*—Obtuse, deep, depth from shoulder 28 mm, breadth at shoulder 30 mm.
*Basin.*—Symmetrical, abrupt at base, wide, depth, 12 mm, width 20 mm.
*Calyx.*—Open, segments persistent, erect, outer and inner surfaces pubescent, triangular in shape, width 4 mm, length 7 mm, color Yellow Green 146 B.

Skin:
*Thickness.*—Thin.
*Texture.*—Very smooth, glossy with medium cuticle wax.
*Tendency to crack.*—Can crack at the stem in high rain conditions at maturity.
*Lenticels.*—Inconspicuous, width 0.1 mm, length 0.1 mm, density 1 per square cm, color Grayed Yellow 164 B.
*Color.*—Yellow 11 B.
*Ground color.*—Very slight blush of Yellow Green 145 A at stem and calyx.

Flesh:
*Aroma.*—Sweet, aromatic, juicy.
*Flesh oxidation.*—Very slow.
*Color.*—Yellow 11 D.
*Texture.*—Very firm, crisp.
*Eating quality.*—Best.

Core:
*Bundle area.*—Medium to ovate, cordate, symmetrical at base.
*Bundle.*—Inconspicuous, alternate above stamens.
*Capillary area.*—Distinct, medium size.
*Calyx tube.*—Urn shaped, closed.
*Seed cells.*—Walls thin, tough, length 14 mm, breadth 8 mm.
*Longitudinal section.*—Broadly ovate.

Seeds:
Number perfect, 6 to 10.
*Number in one cell.*—1 to 2.
*Length.*—7 mm.
*Breadth.*—5 mm.
*Form.*—Obtuse, non-tufted.
*Color.*—Grayed-Purple 183 A.

Stem:
*Length.*—39 mm.
*Width.*—3 mm at junction with apple, 7 mm at abscission layer with spur.
*Color.*—Grayed Yellow 160 A with slight blush of Grayed Orange 167 A.

Use: Processing, fresh market, dessert.

Shipping quality: Good, subject to stem puncture.

Keeping quality: Excellent, 3 to 6 months in common storage.

Tree winter hardiness: Average for an apple variety. Tree is hardy to −20° C. to 25° F.

Bud winter hardiness: −15° to −20° F., depending on the stage of development of the bud.

Drought tolerance: Average for an apple variety. Normal requirements average ¼" of rain per week. Severe drought adversely affects fruit size and quality.

Disease resistance: Susceptible to fire blight (*Erwinia amylovora*) and other bacterial diseases. Moderately susceptible to apple scab (*Venturia inaequalis*), powdery mildew (*Podosphaera leucotricha*), and other fungal diseases.

I claim:

1. A new and distinct variety of apple tree, *Malus domestica,* substantially as herein shown and described.

FIG. 1/3
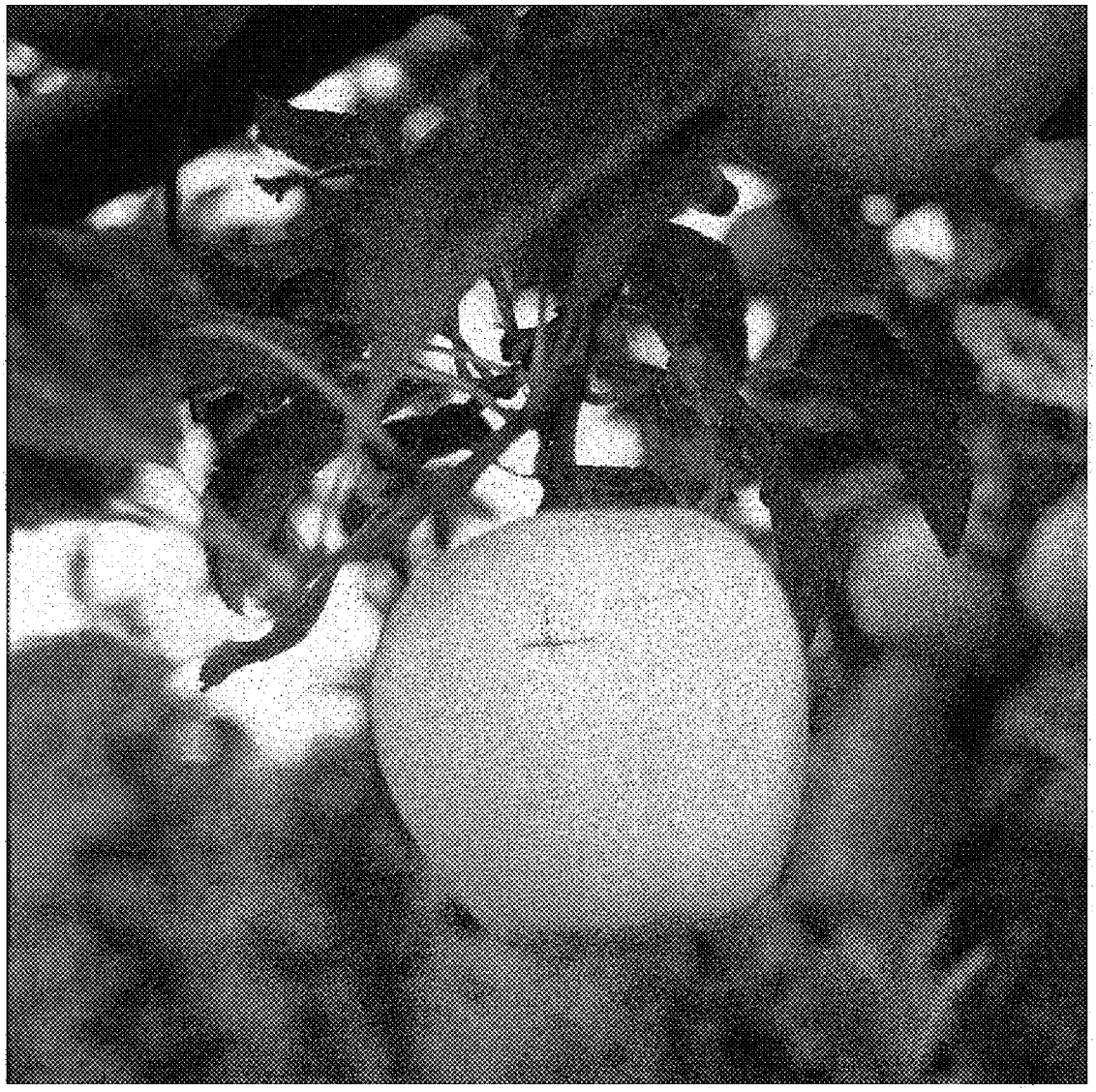

FIG. 2/3
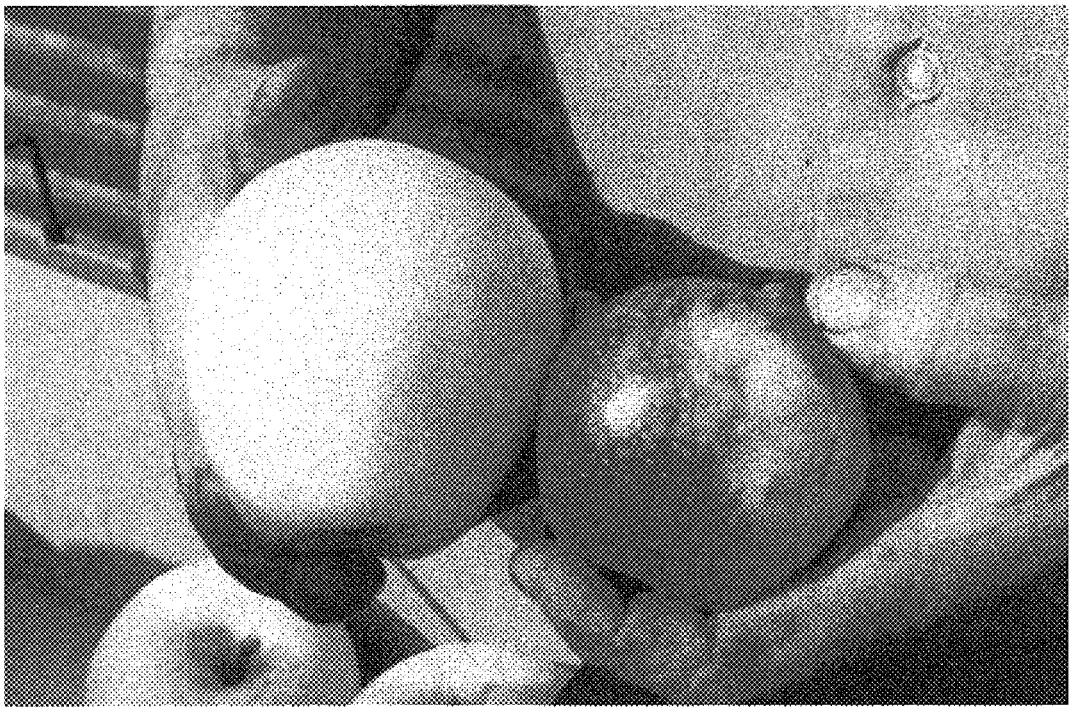

FIG. 3/3
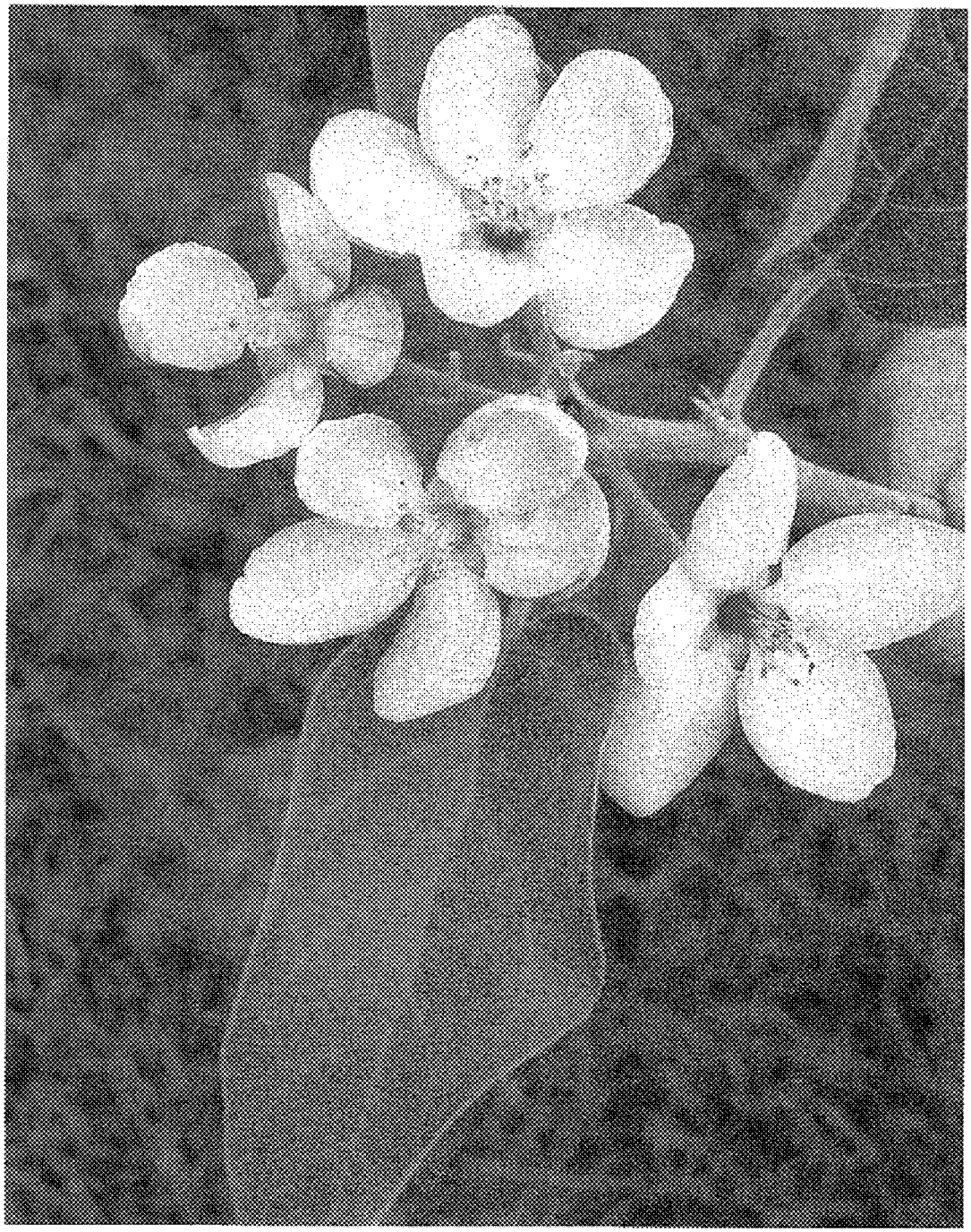

* * * * *